United States Patent [19]
Bergersen

[11] 3,950,851

[45] Apr. 20, 1976

[54] ORTHODONTIC POSITIONER AND METHOD FOR IMPROVING RETENTION OF TOOTH ALIGNMENT THEREWITH

[76] Inventor: Earl O. Bergersen, 950 Linden Ave., Winnetka, Ill. 60093

[22] Filed: Mar. 5, 1975

[21] Appl. No.: 555,553

[52] U.S. Cl. ............................................. 32/14 B
[51] Int. Cl.² ........................................ A61C 7/00
[58] Field of Search ............ 32/14 C, 14 B; 128/136

[56] References Cited
UNITED STATES PATENTS
| | | | |
|---|---|---|---|
| 2,467,432 | 4/1949 | Kesling | 32/14 B |
| 3,178,820 | 4/1965 | Kesling | 32/14 C |

*Primary Examiner*—Robert Peshock
*Attorney, Agent, or Firm*—Larson, Taylor and Hinds

[57] ABSTRACT

After a patient's teeth have become substantially perfectly aligned by a custom or preformed positioner, one or more selected depressions are filled with a liner material in a soft moldable state and having the property of hardening over a short period of time at body temperature and adhering to the positioner surface. The positioner is then placed in a patient's mouth with the teeth in place within their respective depressions. The filling material in the selected depressions then forms the outer contour of the teeth located therein and hardens, thereby providing in those depressions inner surfaces precisely fitted to the contour of their respective teeth.

16 Claims, 10 Drawing Figures

ORTHODONTIC POSITIONER AND METHOD FOR IMPROVING RETENTION OF TOOTH ALIGNMENT THEREWITH

BACKGROUND OF THE INVENTION

This invention relates to tooth positioning appliances, and in particular it relates to improvements in such appliances for enhancing retention of tooth alignment.

In the field of orthodontics, conventional orthodontic devices such as bands or the like are often used for straightening teeth to bring them to a predetermined position or close to proper occlusion. To bring the teeth into a final position of desired orientation in the mouth, the orthodontist will often use a tooth positioner One type of positioner which is custom-made for each individual patient is illustrated in the Kesling U.S. Pat. No. 2,467,432. Another type of positioner which is preformed in a limited number of sizes, and wherein the patient is fitted with the correct one of the limited number of sizes is shown in my Canadian Patent No. 897,464, issued Apr. 11, 1972.

One problem which has been encountered in the use of this type of positioner is that when the teeth are properly aligned or essentially so, there is a tendency for the patient to reduce his enthusiasm for cooperation, as a result of which the essentially perfect result achieved at this point starts to relapse slightly as cooperation lags. Hence, there exists a need for providing improvements in the art relating to orthodontic positioners of the the present type which will enhance retention of tooth alignment through all stages of use thereof.

SUMMARY OF THE INVENTION

Thus, it is a purpose of the present invention to provide improvements in orthodontic positioners of the type described which will overcome the above described disadvantages which have existed heretofore.

This purpose of the present invention is achieved by modifying the inner surfaces of the positioner, after it has been used to bring the teeth into a desired alignment, by reshaping selected tooth depressions exactly to the outer contour of their respective teeth, to thereby firmly hold those selected teeth in a precise position.

In accordance with a preferred embodiment, this reshaping is accomplished by introducing into the selected depressions a soft moldable material which has the property of hardening at body temperature after a short period of time and adhering permanently to the positioner itself. With this material, the positioner is placed into the patient's mouth, centered properly therein, and the patient is asked to close his teeth and hold them together for a few minutes until the material hardens. The positioner is then removed and when the material has completely hardened it is trimmed at the margins of the tooth depressions. As a result, there is provided a tooth positioner originally preformed or custom-made for the purpose of moving teeth to a desired position, and further including a liner material within selected tooth depressions, which liner is shaped essentially precisely to the outer contour of the tooth received therein, thereby firmly holding this tooth in the position which it has reached up to this point. The present invention is applicable of course to either a maxillary positioner, a mandibular positioner or a combined maxillary-mandibular positioner. In the latter case, it is preferable although not absolutely necessary to work with one half of the positioner at a time, first reshaping the depressions on either the upper to the lower half, and then subsequently reshaping the depressions on the other half.

The material of the liner may be one that becomes relatively hard at body temperature or one which is relatively resilient or rubber-like at body temperature. If a hard material is used, it has the advantage that the positioner will snap in place quite firmly as the occlusal surfaces of the teeth move into their respective depressions, pushing aside the hard material at the gingival edges of the depressions which are provided for pressing against the undercut portions of the teeth adjacent the gums when the teeth are firmly in place in their respective depressions. Alternatively, if the liner material is relatively resilient, it might not have the same firm positive action as with a harder material but apparently with a resilient material it is possible to more closely and precisely fit the outer contour of the teeth. Indeed, the advantages of both the hard and the soft materials can be achieved in a single embodiment utilizing a material which is hard at body and room temperature but which becomes rubbery a few degrees thereaove. This material can have the advantages of both in that the patient can warm the finished relined positioner in hot water, place it in his mouth after which it will slowly harden and function like the hard liner material by firmly holding the teeth in place.

Many materials are known which could be utilized to form the liner material. Preferably, materials would be used which would polymerize chemically bond with or otherwise strongly adhere to the material of the positioner itself or with an additional material applied thereto for that purpose. For example, the preformed or custom positioner could be made of a polymer or copolymer of the same material or of a material one which would provide an adhering surface for the insert material. This might include for example a material with a small percentage by weight of acrylic resin which would thus provide a perfect adhering surface for a self-cure acrylic polymer which would remain permanently attached thereto. A methyl-methacrylate monomer may be painted on the surface of the positioner where the liner material is to be added, after which this monomer and the self-cure acrylic polymer are mixed into a runny consistency and placed onto the said painted surface. With the positioner in this state, the positioner would be placed into the patient's mouth, centered properly, and the patient would be asked to close his teeth and hold them together for a couple of minutes until the material hardens. After hardening, the material would be trimmed and polished.

Thus, it is an object of the present invention to provide an orthodontic positioner of the type described, with certain portions thereof reshaped so as to retain retention of a previously attained tooth alignment.

It is another object of this invention to provide a method for utilizing an orthodontic positioner so as to enhance retention of tooth alignment, said method including first utilizing the positioner for a predetermined period of time so as to achieve a desired, preferably perfect, alignment of the teeth, and then reshaping the interior of certain tooth depressions so as to precisely and firmly adapt to the outer contour of their respective teeth.

Other objects and advantages of the present invention will become apparent from the detailed description to follow, together with the accompanying drawings.

BRIEF DESCRIPTION OF THE DRAWINGS

There follows a detailed description of preferred embodiments of the present invention which are to be read together with the accompanying drawings which are provided for the purpose of illustrating preferred embodiments of the invention.

DETAILED DESCRIPTION OF THE PREFERRED EMBODIMENTS

Figure 1:
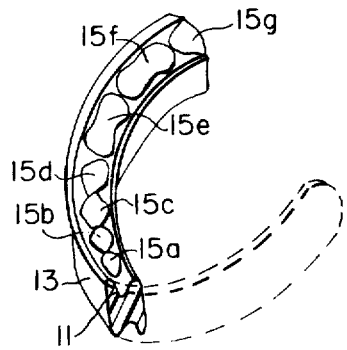
FIG. 1 is a perspective view showing a conventional preformed or custom-made positioner.

Referring now to the drawings, like elements are represented by like numerals throughout the several views.

FIG. 1 illustrates a conventional preformed or custom positioner of the type with which the present invention is concerned. After the bands have been removed a positioner of this type is used to effect limited final movement of the teeth and then to retain those teeth in that final position. To accomplish this, the positioner 10 has formed between a labial-buccal flange 13 and a lingual flange 14 upper and lower troughs 11 and 12, each of which have tooth depressions therein. The depressions starting with the right lateral incisor back to the second molar are represented by numerals 15a through 15g. Similarly, depressions for the lower teeth would be formed into the trough 12. Alternatively, positioners can be provided which are solely for the mandibular teeth or solely for the maxillary teeth. In any event, these depressions as represented in FIG. 1 by 15a through 15g are shaped so as to actually exert a physical moving force upon a tooth received therein so as to move to a selected final position of alignment. To accomplish, the positioner must of course engage the tooth at one point and be free of engagement with that tooth at at least some other points on the contour of that tooth.

The difficulty then arises at that point in time wherein tooth movement has been completed so as to bring the teeth into an essentially perfect alignment. At this point there is a clear tendency for the patient to reduce his enthusiasm, the consequence of this being the commencement of relapse.

The present invention overcomes this problem by providing in certain selected tooth depressions a liner material which in essence reshapes that depression so as to essentially exactly fit the outer contour of the tooth received therein. This is in contrast to the original shape of each depression wherein there was normally a space between the inner surfaces of the depression and at least some surfaces of the teeth. One important portion of the liner is that which mates with the undercut portion of the tooth adjacent the gum. Prior to the reshaping of the present invention, the surfaces of the depression tended to move straight towards the gum so as to not block movement of the occlusal edges of the tooth into and out of the depression. With the present invention, however, there will be this new portion adjacent the outer edges of the depression adapted to mate with the undercut portion of the teeth adjacent the gum and hence possibly blocking movement of the larger occlusal edges of the teeth into that depression. The result will be that to move that tooth into the depression it will have to move aside these said portions of the liner adapted to mate with the undercut portions of the teeth, these latter portions then snapping back into place after the tooth has completed its movement into the depression, whereby the liner material firmly engages the tooth to hold it firmly in that specific position.

Figure 2:
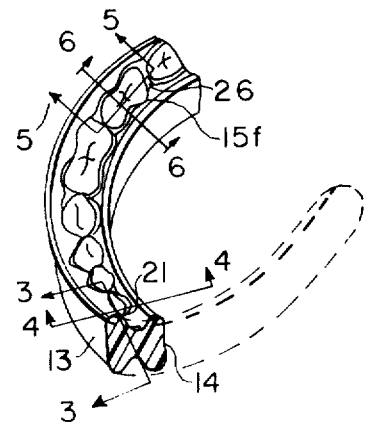
FIG. 2 is a perspective view similar to FIG. 1 but showing the positioner of FIG. 1 modified to include the features of the present invention.

FIG. 2 illustrates the positioner of FIG. 1 wherein the depressions include the liner material therein which exactly mates to the outer contour of the teeth. While FIG. 2 illustrates all of the visible depressions as having liner material therein, it will be understood that the concept of reshaping the depressions can be applied to a single depression or to any combination of tooth depressions. In some cases it may be preferable to reshape only the anterior tooth receiving depressions although the invention of course encompasses reshaping any one or any combination of depressions.

Although the preceding discussion has concerned itself primarily with the end result of filling in the tooth depressions, in practice the procedure can be relatively simplified by proceeding in a manner wherein an entire trough such as the upper trough 11 can be filled with the soft moldable material as the positioner is placed into the patient's mouth. As the patient then occluded his teeth, excess material would move not only into that portion of the trough above the depressions, but possibly also up over the edges of flanges 13 and 14. The positioner is preferably removed from the patient's mouth after the liner material has hardened slightly but before it has completely hardened. In this state the material is preferably still sufficiently soft that it can be easily trimmed from the areas above the depressions with a suitable cutting instrument.

Figure 3:
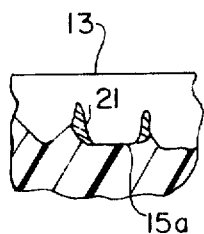
FIG. 3 is an enlarged partial cross-sectional view taken in the mesio-distal plane as represented by the line 3—3 in FIG. 2, and showing a tooth depression including a liner in accordance with the present invention.
Figure 3A:
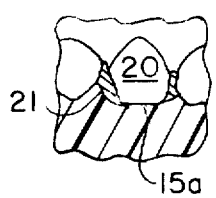
FIG. 3A is a view similar to FIG. 3 but showing the same tooth depression with its respective tooth received therein.
Figure 4:
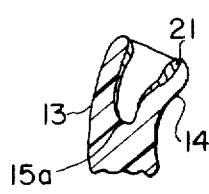
FIG. 4 is an enlarged partial cross-sectional view of the same tooth as FIGS. 3 and 3A but taken in the labial-lingual direction as indicated by line 4—4 in FIG. 2.
Figure 4A:
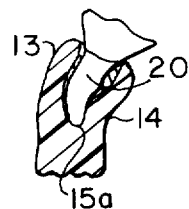
FIG. 4A is a view similar to FIG. 4 but showing the same tooth depression with its respective tooth received therein.

FIGS. 2 through 6 illustrate the positioner of FIG. 1 modified with all of the upper tooth receiving depressions relined to precisely fit the outer contours of their respective upper teeth. FIGS. 3 and 4 illustrate the upper lateral incisor tooth depression 15a with the liner material 21 therein. In FIG. 3 the liner material 21 is shown as it might extend slightly up into the space between this tooth and its adjacent tooth while FIG. 4 illutrates how the material might run up to the upper edge of depression 15a so as to mate with the undercut portions of the labial and lingual sides of the tooth. FIGS. 3A and 4A then illustrate this modified depression of FIGS. 3 and 4 with a lateral incisor tooth 20 located therein.

Figure 5:
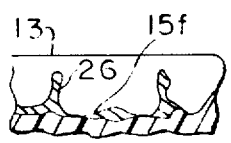
FIG. 5 is an enlarged partial sectional view of a molar tooth depression and taken in the mesio-distal direction, as indicated by the line 5—5 of FIG. 2.
Figure 5A:
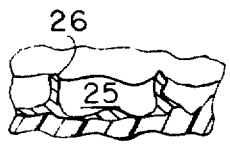
FIG. 5A is a view similar to FIG. 5 but showing the same tooth depression with its respective tooth received therein.
Figures 6, 6A:
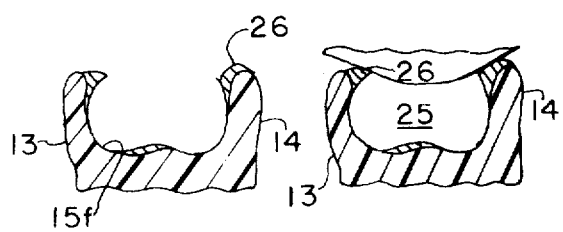
FIG. 6 is a view of the same tooth depression as in FIGS. 5 and 5A but taken in the bucco-lingual direction as indicated by the line 6—6 in FIG. 2.
FIG. 6A is a view similar to FIG. 6 but showing the same tooth depression with its respective tooth received therein.

FIGS. 5 and 6 illustrate the molar tooth depression 15f with the liner material 26 therein. FIGS. 5A and 6A illustrate how the liner material closely adapts to the outer surfaces, and in particular the undercut portions of molar tooth 25.

The liner may be formed of any material which can initially be formed into a soft moldable state and which will harden after a short period of time and firmly adhere to the surface of the positioner itself. "Harden" in this sense may include a very stiff consistency or a rubber-like consistency. Alternatively, a material may be selected which is very stiff at room and body temperature but which becomes slightly rubber-like a few degrees thereabove. One specific material, vinyl-acrylic copolymers, were mentioned above. Another preferable material is silicone rubber. However, there are of course numerous other materials which would strongly adhere to the positioner itself, preferably by polymerizing therewith. For example, a monomer can be applied to the surface of the substrate with a copolymer thereover of essentially the same material as the monomer or the positioner so as to cause polymerization therebetween. In any event, these techniques are well known in the chemical arts so that a further detailed description thereof is not necessary. In any event, since the liner will have been added at a later point in time then the actual formation of the positioner, its molecular structure will tend to form a line of demarcation with the surface of the positioner so that if one views a cross-section cut through both the liner and the material, it will be evident that they constitute phases which are discontinuous at their interface so that the liner can be said to form a discontinuous phase with the material of the positioner itself.

Although the invention has been described in considerable detail with respect to preferred embodiments thereof, it will be apparent that the invention is capable of numerous modifications and variations apparent to those skilled in the art without departing from the spirit and scope of the invention.

I claim:

1. A method of fitting an orthodontic tooth positioning appliance to a patient, comprising the steps of:
   fitting a patient with an orthodontic tooth positioning appliance of the type which is generally U-shaped in plan view and which has a tooth receiving trough generally of a size and shape for reception of the teeth of a patient for correcting the positioning of at least some of the patient's teeth, and
   after a period of wear of the appliance by the patient in which a desired position of the teeth have been reached, positively fixing the position of one or more selected teeth relative to the positioner by filling in the depressions of the one or more selected teeth with a liner shaped substantially precisely to the outer contour of the respective tooth of that liner sufficiently to hold its respective tooth in said desired position relative to the positioner.

2. The method of claim 1, said filling step comprising inserting in each said depression a soft moldable material which hardens at room temperature and which has the property of adhering to the surface of its respective depression, placing the positioner into the patient's mouth such that the selected one or more teeth enter the said filling material in their respective depressions to form an impression therein substantially precisely of the outer contour of the tooth therein, and allowing the material to harden while in the patient's mouth.

3. The method of claim 2, wherein the filling material is formed at least in part of the same material as the original positioner.

4. The method of claim 2, said positioner being a vinyl-acrylic copolymer, and the filling material being a self-cure acrylic resin.

5. The method of claim 2, said filling material being a silicone rubber.

6. The method of claim 2, said inserting step further comprising painting the interior of the one or more selected depressions with a monomer and applying said filling material as a mixture of said monomer and a polymer of a viscous consistency into the depressions over the painting monomer.

7. The method of claim 6, said positioner being a vinyl-acrylic copolymer, said monomer being methyl-methacrylate, and said filling material being a mixture of said methyl-methacrylate monomer and an acrylic copolymer.

8. The method according to claim 2, including forming said liner in at least the anterior teeth of the positioner.

9. An orthodontic tooth positioning and retaining appliance which is generally U-shaped in plan view and which has a tooth receiving trough generally of a size and shape for reception of a patient's teeth, said trough being of an elastomeric material, and said trough having one or more selected depressions therein shaped substantially precisely to the outer contour of its respective tooth sufficiently to hold its respective tooth in a fixed position relative to the positioner,
   said positioner comprising a substrate in the shape of a conventional positioner shaped to correct and retain teeth within the patient's mouth, and including a liner forming a discontinuous phase with respect to the substrate within the selected one or more depressions to form the portion of outer contour of the said selected teeth.

10. An orthodontic appliance according to claim 9, said substrate being a vinyl-acrylic copolymer, and said liner being an acrylic resin.

11. An orthodontic appliance according to claim 9, said substrate being a vinyl-acrylic copolymer and said liner being silicone rubber.

12. An orthodontic appliance according to claim 9, said positioner including both an upper maxillary trough and a lower mandibular trough, and including at least some of said selected depressions in both the upper and the lower troughs.

13. An orthodontic positioner according to claim 12, said selected upper and lower depressions including the anterior tooth receiving depressions.

14. An orthodontic appliance according to claim 9, said liner being of a material which is stiff at body temperature.

15. An orthodontic appliance according to claim 9, said liner being of a material which is resilient at body temperature.

16. An orthodontic appliance according to claim 9, said liner being of a material which is stiff at body temperature and which becomes resilient when heated slightly above body temperature.

* * * * *